United States Patent [19]

Herman

[11] Patent Number: 5,113,876
[45] Date of Patent: May 19, 1992

[54] SKELETAL STABILIZATION APPARATUS FOR USE IN TRANSPORTING AND TREATING PATIENTS AND METHODS THEREFOR

[76] Inventor: John A. Herman, 16 Hewes St., Port Jefferson Station, N.Y. 11776

[21] Appl. No.: 514,697

[22] Filed: Apr. 26, 1990

[51] Int. Cl.⁵ .............................................. A61F 5/37
[52] U.S. Cl. ..................................... 128/870; 24/590; 24/702; 602/18
[58] Field of Search ................. 128/870, 871, 876, 78, 128/87 B; 24/702, 669, 615, 590, 593, 595

[56] References Cited

U.S. PATENT DOCUMENTS

| | | | |
|---|---|---|---|
| 2,591,925 | 4/1952 | Erbe | 24/702 X |
| 3,889,668 | 6/1975 | Ochs et al. | 128/875 X |
| 4,252,113 | 2/1981 | Scire | 128/870 X |
| 4,519,106 | 5/1985 | Sandquist | 128/876 X |
| 4,539,736 | 9/1985 | Yokosuka | 24/702 X |
| 4,895,173 | 1/1990 | Brault et al. | 128/876 X |

Primary Examiner—Robert A. Hafer
Assistant Examiner—Kevin G. Rooney
Attorney, Agent, or Firm—Brooks Haidt Haffner & Delahunty

[57] ABSTRACT

Apparatus for skeletal stabilization of patients for transportation, treatment, and diagnosis, which apparatus comprises a radiolucent board having T-slots opposite each other at intervals along the long edge of the rectangular board and radiolucent straps having at one end a structure adapted to be fitted into a T-slot and secured there, and having at the other end fastening means for holding that end to another strap, together with methods for stabilizing patients using such apparatus and radiolucent straps for such apparatus and methods.

10 Claims, 6 Drawing Sheets

SKELETAL STABILIZATION APPARATUS FOR USE IN TRANSPORTING AND TREATING PATIENTS AND METHODS THEREFOR

BACKGROUND OF THE INVENTION

The present invention relates to novel apparatus and methods for stabilizing patients so that they can readily be transported and/or treated, and more particularly, it relates to apparatus for securing patients and accident victims to back boards, cots, stretchers and the like and to methods therefor.

There are many instances in caring for patients when it is highly desirable that the patient be stabilized and that selected musculoskeletal regions be immobilized to avoid and/or minimize any trauma associated with removing the patient from a hazardous area, such as a fireground, or from an accident or other scene, and safely transporting the patient to a medical care facility. One of the desiderata is that the patient be securely fastened to and/or restrained to a stable surface to aid in transportation and treatment. Thus, a patient who is involved in a vehicular accident may be trapped in the conveyance, and part of the rescue operation will entail stabilizing the patient so that removal from the primary site of the trauma will cause a minimum of, and preferably no, further injury to the patient.

In the field, it is frequently not possible for the emergency medical technician, fireman, policeman, or other rescuer immediately to determine the nature of the patient's injuries. It is, however, usually necessary that the patient be rapidly and safely removed from the conveyance or other situation. The need is particularly acute in a situation such as a vehicular or structural fire, when only a very limited time is available to remove the patient from a life-threatening situation.

One common appliance used in such situations is the so-called "back board" or "spinal board."

Conventional boards generally contain a plurality of oblong slots which can serve as hand-holds for carrying the boards. One slots to allow for fastening straps to the boards. The fastening straps are held by metal attachments to the pins. These metal attachments for the straps are usually clip- or hook-style quick connect metal fittings. One difficulty encountered with such construction is that the boards are generally about three-quarters of an inch in thickness, so that there is not a great thickness of board material to hold a, say, one-quarter inch pin in place across the slot. Thus, under heavy loading (which can occur at the most crucial time in moving a patient), the pin can pull through the remaining thickness of the board with very serious consequences to the patient and to the rescuers. Indeed, such pins generally cannot be used at all in molded plastic boards or fiberglass-reinforced boards.

Such spinal boards conventionally comprise a piece of stiff plywood or other rigid material containing generally rectangular apertures. The apertures are spaced from the edges of the board so that straps can be riven through the slots to be passed around the board and through a second slot to secure the patient to the board. Conventionally, auto seat belts are used to secure the patient to the board. In earlier days, such belts relied on metal-to-fabric friction to secure the two ends of the belt to each other. Latterly, the belts utilize a metal-to-metal fastener wherein one end of the belt contains a flat member which inserts into a buckle and can be locked into place to secure the two ends of the belt, and thus secure the patient to the board. Various other means of joinder are available in various products. Examples of these are cam buckles, D-rings, triple slides and the like.

Such fastenings are readily available and do a satisfactory job of securing a patient to the board. One of the precepts followed in treating trauma and other patients is that movement be minimized, so that any injury is not aggravated by handling. It is thus desirable that the patient undergo any further preliminary evaluation and treatment, such as obtaining roentgenograms before removal from the backboard. Unfortunately, the conventional belts rely on metal fasteners, and these frequently interfere with roentgenography and other imaging techniques, so that the straps may need to be released and removed with consequent possible movement of and further injury to the patient. Moreover, conventional quick-connect metal fasteners can injure the patient or the rescue worker if they come adrift and flail during emplacement or removal.

THE INVENTION

The present invention provides improved equipment and methods for skeletal stabilization of patients by enabling a patient to be securely fastened to backboards or spinal boards. These improvements are accomplished with no protruding metal pins or other fittings which can constitute a point of weakness or potential failure or interfere with use of the spinal board. The invention provides a system which need not use any metal fittings and which is accordingly substantially radiotransparent or radiolucent and which is neutral in other imaging techniques such as ultrasound and nuclear magnetic resonance imaging techniques, so that the patient can remain stabilized on the board without hindrance to roentgenography or other imaging techniques necessary or desirable for diagnostic purposes.

Briefly, the present invention provides a method which uses a board, having T-slots cut in or near the lateral edges of the board, in conjunction with a non-metallic strap, such as a nylon web strap, being enlarged and of substantially the full width at the very end, but being necked-down at a first end of the strap, so that such end of the strap can be inserted edgewise into the viser, or base, of the T-slot, turned and rotated into the head, or top, of the T, and pulled so that a bolus or enlargement at the end of the strap rests against the head of the slot, thereby securing the strap against movement out of the T-slot. The other end of the strap from the first end has a means for fastening the strap to a similar end of a second strap, the other strap having a first end substantially like that of the first strap. One method for skeletal stabilization according to the present invention accordingly comprises placing a patient on the board having T-slots, securing a first strap to the board by inserting the neck of the strap into the riser of the T, moving the strap toward the head of the T and rotating the strap to move the reduced-width portion near the end across the head of the T, and pulling the strap to tighten the enlarged end into the head of the T. Thereafter, another strap is attached to a T-slot on the opposite side of the board and the two loose ends of the straps are attached by fastening means, thereby to maintain the patient securely to the board. Further articles and methods are hereinafter disclosed.

The invention will be further described by reference to the accompanying drawings, wherein.

The article which provides the base and stiffness to the apparatus of this invention is a generally planar board. "Board" will herein be understood to mean a relatively stiff member, and it will be further understood by those skilled in the art from the present disclosure that it can be constructed of any stable material, including a natural material such as wood, plywood, particle board or the like, or of a synthetic material. Thus, the board can be molded of a thermosetting or thermoplastic material or of another moldable material which will have the requisite stiffness and which can be molded to the desired shape and size. The board can be built up in layers of wood to form laminate structure or it can be built up from fiberglass or polyolefin or other fibrous mat or roving and saturated with a thermosetting material such as an epoxy to form a composite material, such as fiberglass-reinforced polyester epoxy resin. The board need not be entirely solid and unbroken, so long as it has sufficient strength and safety factor to support a patient being transported, and so long as there is enough material to define the T-slots required for the practice of the method of the present invention.

Thus, it will be understood that the board utilized herein can be comprised of wood, nylon, a polyolefin such as polyethylene or polypropylene and the like, or a composite structure as taught above. One desirable embodiment of the invention uses a material of construction for the board which is capable of providing the requisite strength, while at the same time keeping the weight of the board to a minimum to provide for easier handling by the paramedical and medical personnel or other rescuers who will be transporting the patient and handling further, secondary treatment, testing, and diagnosis of the patient. In certain preferred embodiments of the invention, the board is constructed of three-quarter inch thick plywood, and exterior grade plywood is most preferred because of its resistance to delamination and disintegration in the presence of moisture.

The generally planar board utilized herein will be understood from the present description to have a substantially rectilinear plan shape. That is, opposite sides of the board are generally parallel, as are the heads of the T-slots on opposite edges of the board. One or both extremities of the board can be tapered, and for purposes of practicing the present invention, it will be understood that such stucture is generally rectilinear. Similarly, the two shorter edges of the board need not be exactly parallel, but may also be tapered for aesthetic or practical considerations.

The present invention is particularly directed to replacing the metal pin structure of conventional boards with the T-slot and strap arrangement. It will be apparent that the present invention provides superior strength of the fastening to the board in comparison to the metal pin fittings of the prior art. Further, all of the components of the present system are radiolucent, so there is no need to remove the patient from the boards of the present invention for roentgenographic, magnetic resonance, ultrasonic or other diagnostic or imaging techniques.

It is accordingly preferred in the practice of this invention that all of the fittings on the straps and on the board be radiolucent. For this purpose, the second end of the strap, the end which is not fixed to the board by engagement in the T-slot as described herein, is provided with radiolucent fittings. One preferred method of attaching the second end of each strap which is not affixed to the board to the other strap is side-release Delrin buckles. These come in a variety of styles and sizes. Such buckle assemblies are available from American Cord & Webbing and from ITW Nexus. These buckles are released by pressing on opposite sides to disengage pawls on the male fitting from the interior of the female fitting. In certain preferred embodiments. the strap webbing is two inches wide, and nominal two-inch side release buckles are used.

Skeletal stabilization devices are the subject of study by various government agencies and medical and standards bodies, but no standards for such devices have been firmly established at this time. One organization which is studying the matter with a view toward setting standards is the American Society for Testing Materials (ASTM). There has been some consideration given to requiring use of metal-to-metal contact buckles of the type familiar in automobile seat belts for transportation of patients in emergency vehicles.

If such standards are adopted, the present invention will still afford the advantages contemplated herein. When the patient is being placed on the board according to the present invention, the straps used can be those fitted with radiolucent buckles as described. For transportation, one or more additional straps, as necessary, fitted with metal-to-metal contact buckles can be used, and these can then be removed when vehicular highway transportation has been accomplished and the patient has arrived at a hospital or other secondary care facility. The remaining radiolucent buckles will not interfere with the diagnostic and imaging techniques mentioned herein.

As taught further hereinafter, the present attachment system has a number of advantages and will be recognized by those skilled in the art from the present disclosure as providing means effectively to immobilize a patient as required, depending upon the injuries or suspected injuries suffered by the patient. Thus, the straps and fastenings according to this invention are not only used to immobilize the thoracic and cervical vertebrae, but can also be used with head immobilizers and restraint systems for pediatric use. A further advantage is that the T-slot engaging ends of the straps and the radiolucent fasteners for joining the second ends of the straps are lighter and thus reduce the hazard when a metal buckle is carelessly handled or comes adrift.

In one preferred embodiment of this invention, the strap is thickened at the outer end by insert molding a plug of the desired shape around the end of the strap itself. The end of the belt, two to three inches in one embodiment, is folded over into thirds lengthwise and then punched with a hot punch to hold the fold. The folded end is then inserted into the opening in the insert mold, and plastic is injected into the cavity holding the end of the strap and flows down onto the end of the strap and into the holes punched in the strap. The webbing of the strap is thereby firmly attached to the plastic plug.

In yet another desirable embodiment of this invention, the strap is folded over into thirds lengthwise over the last two to three inches, a molded bolus is placed at the end of the strap, and the bolus is sewn into the end of the folded webbing. The bolus is shaped so as to form the webbing into the selected shape and to give stiffness to the neck of the strap near the end thereof.

Figure 1:
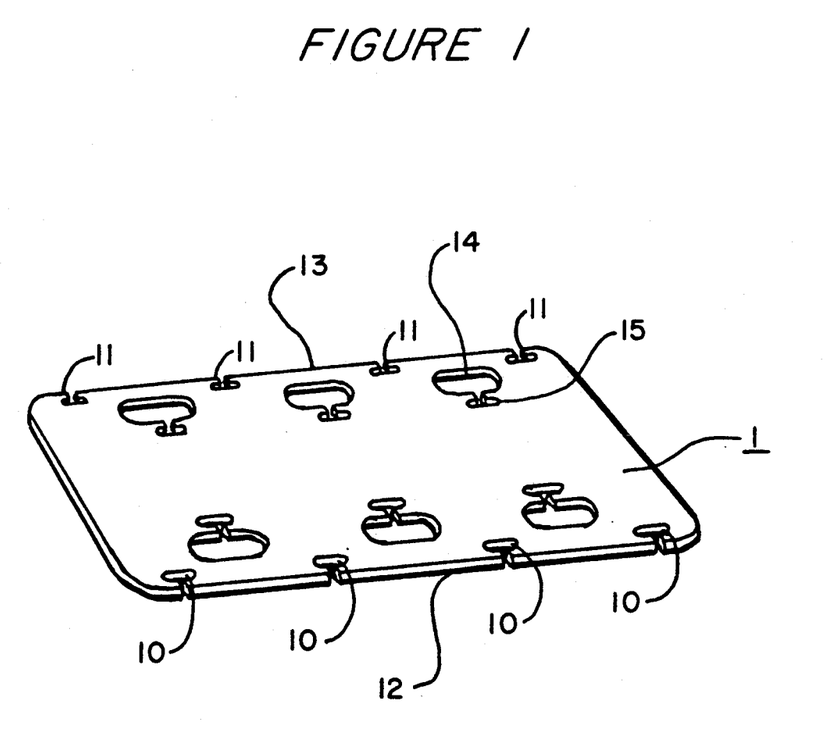
FIG. 1 is a view of a short backboard having defined therein slots which are generally in the shape of a T for use in the practice of the invention.

The invention is further described with reference to FIG. 1 showing a "short board" which is particularly adapted for use in removing accident victims from confined spaces or from areas with restricted access due to tight means for egress. It will be understood by those skilled in the art that the same considerations apply to the construction of long boards, these generally having more slots over the greater length.

Referring to FIG. 1, the edges of spinal board 1 are provided with a plurality of T-slots 10. It will be appreciated by those skilled in the art from the present description that, while a short board is shown with four T-slots in each opposite edge of the longer sides, it is possible to vary the length of the board to make it full-length for average patients, and in this instance it can be useful to increase the number of T-slots to give further security in fastening the patient to the board or further flexibility in placing the straps along the length of the board. If desired, for example, the T-slots can be placed at regular intervals along the length of the board or they can be placed irregularly so that more points are available for fastening at the head and foot areas and few are available for the torso, which is generally less likely to require immobilization.

Board 1 in the embodiment shown would have a length sufficient to support a patient's skeleton from the head to the coccygeal area. For an adult, short board 1 would have a length of 32 inches and a width of 16 inches. Both short boards and long boards have a width of from about 16 to 18 inches in certain desirable embodiments of the invention. Board 1 is provided with four T-slots 10 on first longer side 12 of the board and four T-slots 11 along edge 13 of board 1. As described hereinafter, these T-slots are used to engage the straps according to the invention to the board.

In the embodiment shown, board 1 is also provided with a series of handholds, such as handhold 14, which handholds are also supplied with T-slots, such as T-slot 15 which are generally the same as T-slots 10 and 11.

Figure 2:
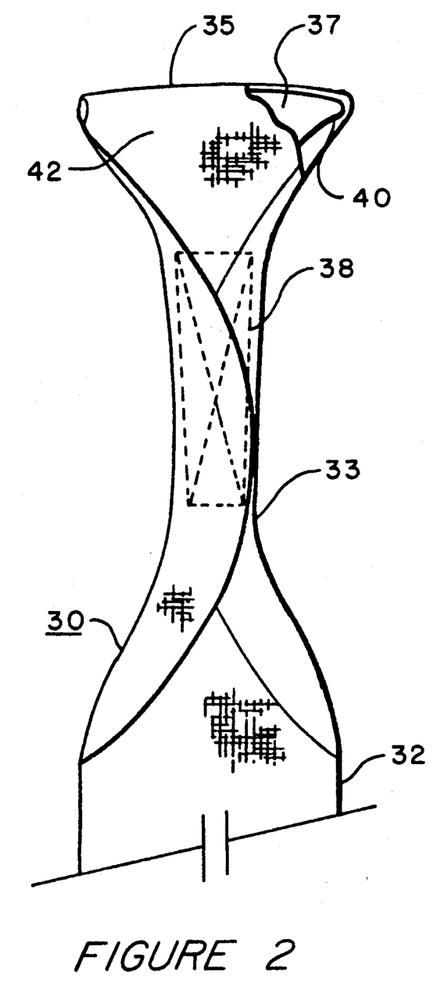
FIG. 2 is a partially cutaway view of the T-slot engaging end of a strap in accordance with the invention.

FIG. 2 shows the T-slot engaging end of strap 30 according to the present invention. In this embodiment, nylon webbing 32 is folded inwardly to the center of the webbing in thirds to form neck 33, and the end is doubled at end 35 over bolus 37. The folded-over end (not shown) and the thirds-folded webbing are secured with box-stitching 38. The bolus is in the shape of a T, with one end 40 of the head, or top, of the T shown at the cutaway. The riser (not shown) of the T of bolus 37 is centered in wide webbing end 42. Thickened end 42, which is substantially the full width of webbing 32, serves to lock the end of the strap into the T-slot as described herein.

Figures 3A, 3B, 3C:
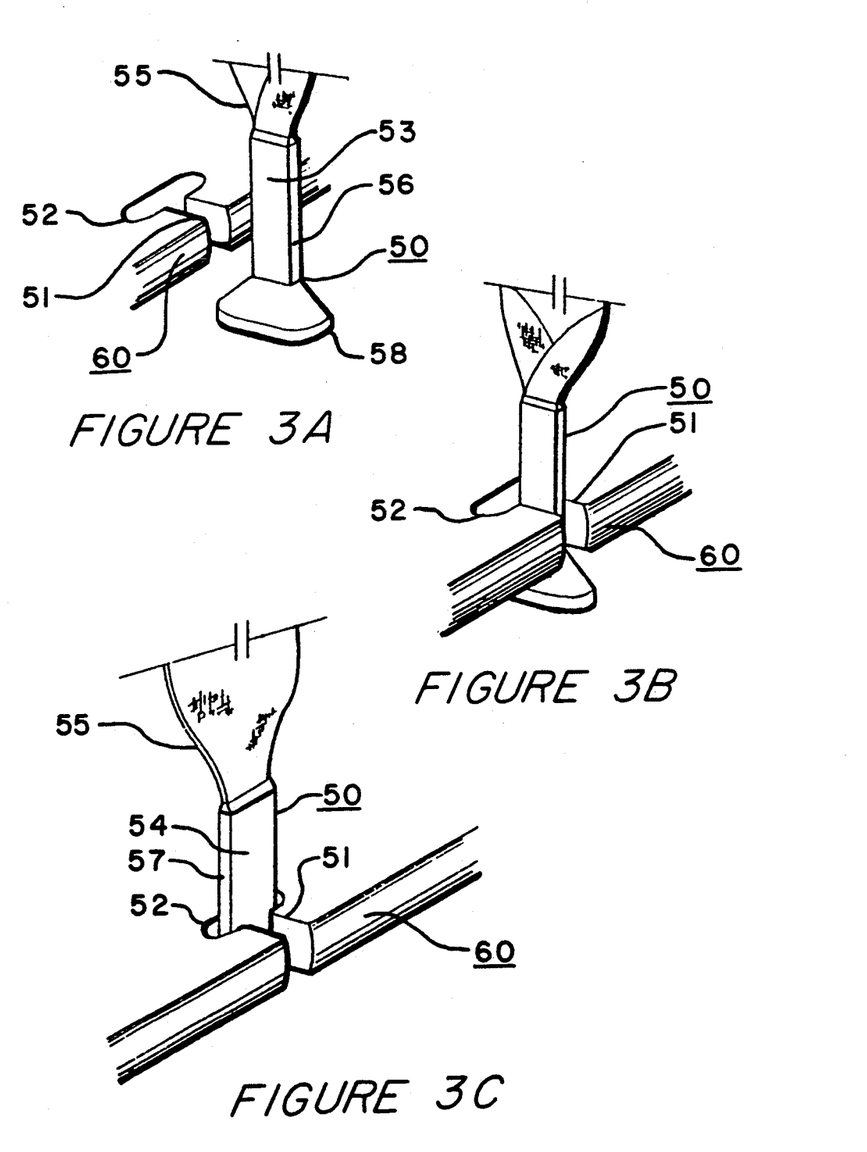
FIGS. 3A, 3B, and 3C are views of another embodiment of the T-slot engaging end of a strap according to the invention, a board.

The embodiment of another form of T-slot engaging end 50 is shown in FIGS. 3A, 3B, and 3C. In this embodiment, T-slot engaging end 50 is also shown ready for insertion into riser 51 of the T slot comprised of riser 51 and head 52 in one of the two edges of board 60. Strap end 50 is formed by folding webbing 55 in thirds and then punching holes in the folded web with a heated die. The folded, punched webbing is then placed in a die and insertion molded with a thermoplastic or thermosetting polymeric material. Finished strap end 50 has a generally rectangular cross section defined on the one side by surface 53 and corresponding surface 54 (seen in FIG. 3C) on the other side and by a thinner surface 56 shown on the near side and corresponding surface 57 (shown in FIG. 3C) on the side opposite thereto. Strap end 50 terminates at the distal end in expanded section 58 which is greater in width and thicker than webbing 55.

FIG. 3B shows end 50 being inserted into riser 51 of the T-slot in board 60. In FIG. 3C belt end 50 has been rotated clockwise so that it rests in head 52 of the T-slot. Webbing 55 is then pulled upwardly to seat end 50 in head 52. The second end (not shown) of webbing 55 is secured to another strap similarly fitted with a termination like end 50 which is secured into another T-slot on the opposite edge of the board. The two free second ends of each strap are then secured to each other by side-release buckles, as described more fully herein. The two straps are thus firmly secured to the T-slots in the board and thereby firmly secure a patient to the board and stabilize the patient's hard tissue against movement during transportation and treatment. It will be understood by those skilled in the art from the present description that strap 30 shown in FIG. 2 can similarly be used to secure the straps and a patient to a board.

Riser 51 of the T-slot is wider than edge 56 to permit entry of end 50 into the riser. Riser 51 of the T-slot is of such a width that the necked-down portion of end 50 can enter the riser and then be rotated 90 degrees into T-slot head 52 so that it is securely fixed. The height of riser 51 is sufficient to leave enough of the board for strength. It will be appreciated by those skilled in the art from the present disclosure that the particular material of construction of the board will have a bearing on the required height of the T riser. The head of the T is wide enough to allow the necked-down section of the strap to fit easily, and the length of the head is short enough to permit the end of the strap to be securely held, caught in the T-slot. The head of the T should be considerably shorter than the width of the strap.

Head 52 is shorter in length than the width of webbing 55, particularly when a T-slot engaging strap 30 is used. In certain desirable embodiments, the length of head 52 is from 33 percent to 50 percent of the width of webbing 55, so that the end 50 is firmly held to board 60. Head 52 has a thickness sufficient to permit side 56 to fit in head 52. If the T-slot engaging end is like that shown in strap end 50, the length of head 52 can be greater, and in certain desirable embodiments is from 95 to 110 percent of the width of webbing 55.

Figure 4:
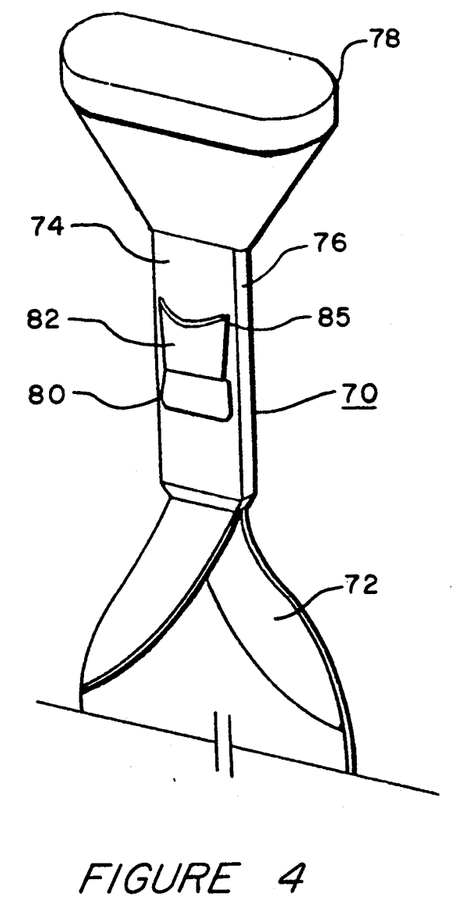
FIG. 4 is a view of a further embodiment of the T-slot engaging end of a strap according to the invention.

FIG. 4 shows another embodiment for the construction of the T-slot engaging end of a strap. Like the FIG. 3 embodiment, webbing 72 is folded and the end of the strap is insertion molded to form strap end 70 comprising surfaces 74 and 76, as well as surfaces 75 and 77

Figure 5A:
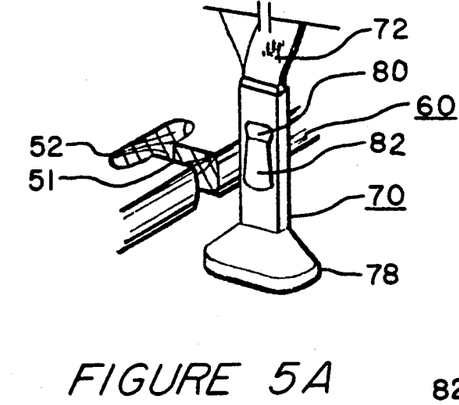
FIGS. 5A, 5B, and 5C are views of the T-slot engaging end of the strap according to FIG. 4 being inserted into a slot and secured to a board.
Figure 5B:
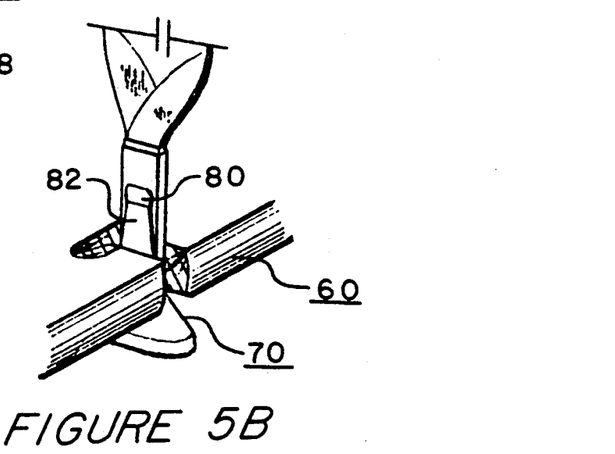
Figure 5C:
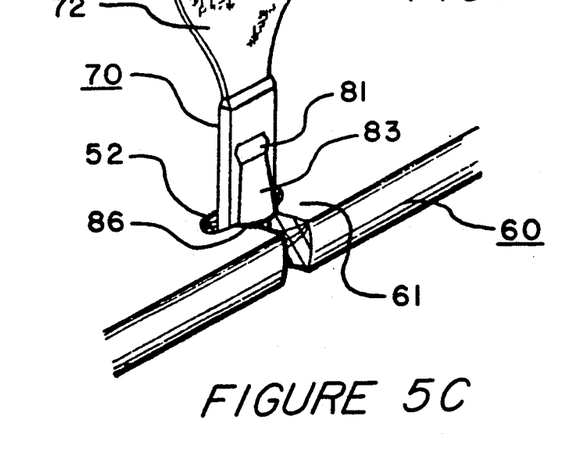

(shown in FIG. 5C). In this preferred embodiment, ears are provided. These are comprised by rigid section 80, which is either adhered to surface 74 or integrally molded as part of surface 74, and flexible outwardly protruding section 82 with engaging surface 85. These ears serve to lock end 78 to a board and thereby hold the end engaged in the T-slot while the second end of the strap is being secured to another strap.

FIGS. 5A, 5B, and 5C show the use of strap end 70 to secure webbing 72 to board 60. FIG. 5A shows end 70 ready for insertion into riser 51 of the T-slot in board 60. In FIG. 5B end 70 has been inserted into riser 51 and flexible ears 82 and 84 are compressed against the larger side 74 and its opposite side so that end 70 can be moved in riser 51. FIG. 5C shows end 70 in head 52 of the T-slot, head 70 having been rotated about the long axis of the strap in a clockwise direction as viewed from above. An upward force has been applied to webbing 72, so that bearing surface 86 has engaged top surface 61 of board 60, as has bearing surface 85 (on the opposite side of end 70 and not shown in FIG. 5C).

Figure 6:
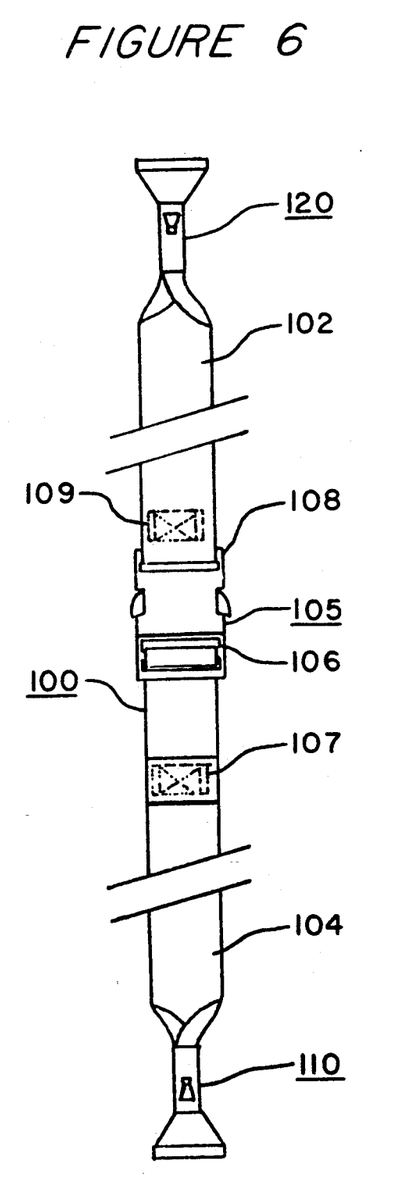
FIG. 6 is a view of an embodiment of a complete strap for use in the practice of the invention.

FIG. 6 shows complete strap assembly 100 according to the present invention. Assembly 100 comprises webbing sections 102 and 104, side release Delrin buckle 105 and strap ends 110 and 120 for insertion into T-slots. Ends 110 and 120 are the same as insertion molded strap end 70 with ears as described herein. Strap 104 wraps around the fitting 106 on the male component of buckle 105 and is secured by box-stitching 107. Similarly, the component of buckle 105 and is secured by box-stitching 109.

The ends of the straps opposite to the ends inserted into the T-slots can be fastened by other means, including loop-and-hook fasteners, such as Velcro. The use of fastening methods such as Velcro may in some cases be insufficient firmly to secure a patient to board 1, for example, and radiolucent buckles are preferred in certain embodiments of the invention.

The end of the straps secured to the board by means of the T-slot insertion are readily released after tension is removed from the strap, as by loosening the buckle holding the two straps together. The end of the strap inserted in the T-slot is pulled perpendicularly away from the surface of the board to disengage it. The narrowed portion of the strap is then rotated into the riser of the T and pulled outwardly away from the board, so that this is the reverse of the T-slot insertion shown, for instance, in FIGS. 5A, 5B, and 5C. The straps can of course be reused numerous times.

An additional advantage according to the present invention is that the entire thickness of the board is available to provide strength and resist stress on the strap. Thus, the construction of such backboards is simplified and improved.

The T-slots can be readily formed in a wooden board, as for instance by routing the shape. Alternatively, the board can be molded of a thermoplastic or thermosetting or other moldable material, and T-slots can readily be provided in such molded products by using an appropriate die configuration.

It will be appreciated by those skilled in the art that variation is permitted. The material of the belt can be on any type which has the requisite strength to maintain a patient securely on the board. Generally, a web belt construction fulfills this requirement. The strap can be made out of any material including natural materials such as cotton, linen, and the like, or from synthetic materials such as polyolefins like polyethylene and polypropylene, polyamides, polyesters, acrylics and the like. In preferred embodiments of the invention, a synthetic fiber webbing strap is utilized. Such straps have superior strength and wear qualities and are easily cleaned. When an insertion molded fitting is used on the strap, the molded plastic and the webbing material must, of course, be compatible.

In another embodiment of the invention, there is provided a cervical stabilization appliance for use in combination with the T-slot-containing board described herein. This cervical stabilization appliance is particularly adapted to the stabilization of the cervical area with the boards according to the present invention in that it is utilized with the T-slots.

Figure 7A:
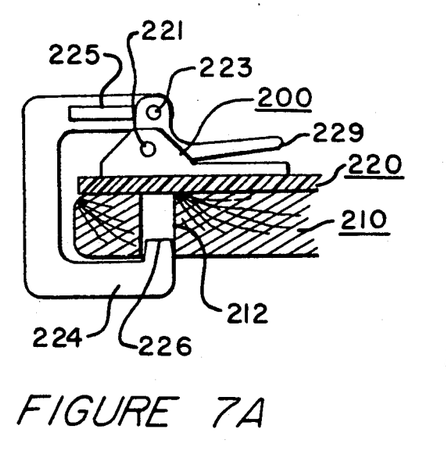
FIGS. 7A and 7B are views of a clamp for use with the cervical stabilization board of FIG. 8 and a board with features as shown in FIG. 1.
Figure 8:
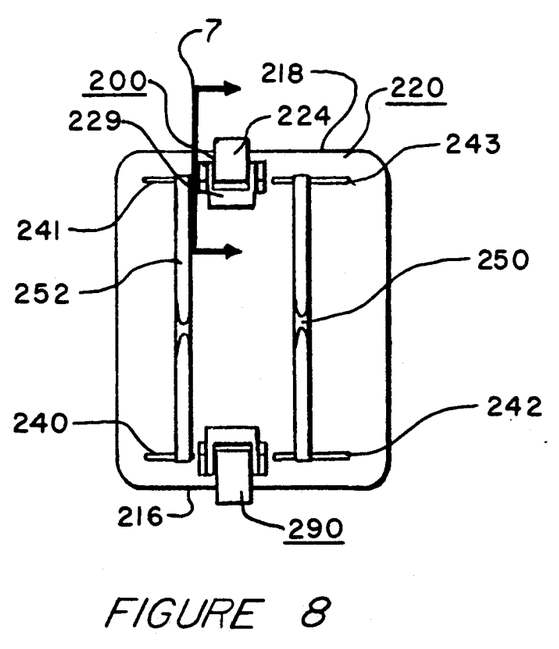
FIG. 8 is a plan view of a cervical stabilization appliance for use with a novel backboard according to another aspect of the invention.

Clamp 200, shown in FIG. 7A, a partial section through cervical stabilization appliance 220 shown in FIG. 8, in the closed, or locked, position, is secured to the base of cervical appliance 220 by means of base 222. Base 222 can readily be held on the board by fastening means (not shown), such as screws, bolts, adhesives, and the like. Release handle 229 is attached to base 222 by hinge pin 221. Handle 229 is in turn secured to gripping member 224 by hinge pin 223. Gripping member 224 is provided with slot 225 so that member 224 is slidable, held by pin 223 to provide for clearance around and emplacement on board 210, which is provided with T-slots, such as those shown on board 1 in FIG. 1.

Figure 7B:
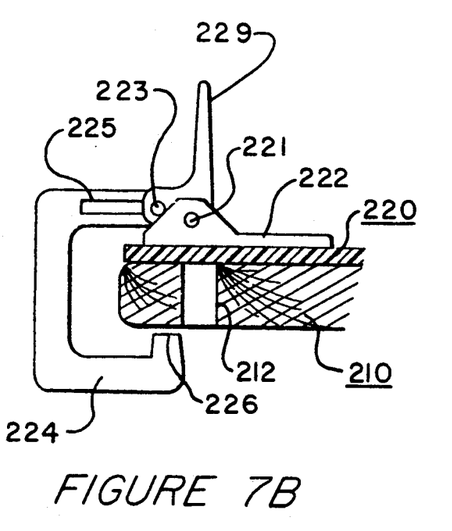

In FIG. 7A, clamp 200 is shown with ridge 226 engaged in head 212 of T-slot 212. This firmly secures cervical appliance 220 to board 210. In FIG. 7B, release handle 229 is shown rotated to the left, thereby disengaging ridge 226 from T-slot head 212 and permitting removal of the cervical stabilization applicance 220 from board 210.

FIG. 8 shows cervical appliance 220 provided with clamp 200 along one edge and clamp 290 at the opposite edge, firmly to secure appliance 220 to a board. Clamps 200 and 290 are shown in the closed position, as they are in FIG. 7A. The base plate of appliance 220 is provided with two preferably non-metallic rails 240 and 241 on one side of the line defined by clamps 200 and 290, and with rails 242 and 243 on the other side of the line. The rails are fitted with straps 250 and 252, which can be fitted with hook-and-loop fasteners, such as Velcro, at each end. Straps 250 and 252, held to appliance 220 by rails 242 and 243 and 240 and 241, respectively, are utilized together with blocks of flexible foam to cushion, stabilize and protect a patient's cervical vertebrae and skull, as will be readily understood from this description by those skilled in the art.

The present invention thus also contemplates and provides cervical stabilization means for use in conjunction with the T-slot-containing boards of this invention. Ridge 226 in certain preferred embodiments of the invention is just slightly shorter in length than the head of a T-slot. This affords additional resistance to longitudinal movement of the cervical stabilization device along the backboard.

What is claimed is:

1. Apparatus for skeletal stabilization of a patient which apparatus comprises in combination a generally planar radiolucent board with a generally rectilinear plan shape and at least one radiolucent strap, the board defining along at least each of two opposite edges at least one slot on each edge, the slot generally having the shape of a T, the strap having first and second ends, the first end being comprised of a section having a width at least equal to the width of the strap at the extreme first end of the strap and being narrower than the width of the strap for a selected distance from the extreme first end, the riser section of the T having a width greater than the thickness of the narrower portion of the strap and the head of the T-slot having a height greater than the thickness of the strap and a length less than the width of the strap, the strap thereby being adapted to be fitted into the head of the T by passing it laterally through the riser section of the T-slot and turning it so that the width of the strap is substantially parallel to the head of the T, the strap thereby being secured from removal from the T so that the strap is secured to the board.

2. Apparatus according to claim 1 wherein the second end of the strap opposite from the end adapted to be fitted into the head of the T-slot is provided with fastening means.

3. Apparatus according to claim 2 comprising a second strap having a first end adapted to be fitted into the head of a T-slot and a second end with fastening means, each first end being secured in a T-slot on a side of the board opposite to the other first end, and the second ends being secured to each other by the fastening means.

4. Apparatus according to claim 1 wherein the width of the narrower portion of the strap is from about 30 percent to about 50 percent of the width of the strap.

5. Apparatus according to claim 1 wherein there are a plurality of T-slots opposite each other at the two longer edges of the board.

6. A cervical stabilization appliance for use with the board of claim 1 which appliance comprises a substantially planar base and at least one clamp comprising a base attached to the planar base of the appliance, a release handle, and a movable gripping member secured to the handle, the gripping member having a ridge for engagement into the head of a T-slot, thereby securing the appliance to the board.

7. A method for skeletal stabilization of a patient which comprises emplacing a patient on the board of claim 1, securing a first strap to one of the T-slots, securing a second strap to a T-slot on the opposite edge of the board, and fastening the second ends of the straps together.

8. Apparatus according to claim 1 wherein the extreme first end of the strap is comprised by a rigid section adhered to the strap, the rigid section at the extreme end of the strap being at least as wide as the width of the strap.

9. Apparatus according to claim 8 wherein the rigid section has ears on the flat side of the rigid section across the width of the strap, the ears being adapted to grip the side of the board opposite to that through which the first end of the strap is inserted to secure the strap to the board against forces acting in the direction toward the end of the strap.

10. A radiolucent webbing strap for skeletal stabilization of a patient by securing the patient to a generally planar radiolucent board with a generally rectilinear plan shape, the board defining along at least each of two opposite edges at least one slot on each edge, the slot generally having the shape of a T, wherein the strap has a first end and a second end, the first end being comprised of a section having a width at least equal to the width of the strap at the extreme first end of the strap and being narrower than the width of the strap for a selected distance from the first extreme end, the narrower section having a width less than the head of the T-slot and a thickness less than the height of the head of the T-slot, the strap thereby being adapted to be fitted into the head of the T by passing it laterally through the riser section of the T-slot and turning it so that the width of the strap is substantially parallel to the head of the T, the strap thereby being secured from removal from the T so that the strap is secured to the board and the second end of the strap comprising fastening means.

* * * * *